(12) United States Patent
Loverich et al.

(10) Patent No.: US 8,348,177 B2
(45) Date of Patent: Jan. 8, 2013

(54) LIQUID DISPENSING APPARATUS USING A PASSIVE LIQUID METERING METHOD

(75) Inventors: Jacob Loverich, State College, PA (US); Jeremy Frank, Pine Grove Mills, PA (US)

(73) Assignee: Davicon Corporation, Mundelein, IL (US)

( * ) Notice: Subject to any disclaimer, the term of this patent is extended or adjusted under 35 U.S.C. 154(b) by 776 days.

(21) Appl. No.: 12/484,589

(22) Filed: Jun. 15, 2009

(65) Prior Publication Data

US 2009/0308945 A1    Dec. 17, 2009

Related U.S. Application Data

(60) Provisional application No. 61/073,275, filed on Jun. 17, 2008.

(51) Int. Cl.
*B05B 1/08* (2006.01)
(52) U.S. Cl. .................. 239/102.1; 239/102.2
(58) Field of Classification Search ............... 239/102.2, 239/102.1, 4, 555
See application file for complete search history.

(56) References Cited

U.S. PATENT DOCUMENTS

| | | |
|---|---|---|
| 2,607,571 A | 8/1952 | Hession |
| 3,543,122 A | 11/1970 | Klebanoff et al. |
| 3,561,444 A | 2/1971 | Boucher |
| 3,615,041 A | 10/1971 | Bischoff |
| 3,690,317 A | 9/1972 | Millman |
| 3,729,138 A | 4/1973 | Tysk |
| 3,738,574 A | 6/1973 | Guntersdorfer et al. |
| 3,765,606 A | 10/1973 | Moss |
| 3,790,079 A | 2/1974 | Berglund et al. |
| 3,804,329 A | 4/1974 | Martner |
| 3,806,100 A | 4/1974 | Cornett, III |
| 3,812,854 A | 5/1974 | Michaels |
| 3,828,357 A | 8/1974 | Koeblitz |
| 3,860,173 A | 1/1975 | Sata |
| 3,861,852 A | 1/1975 | Berger |
| 3,866,831 A | 2/1975 | Denton |

(Continued)

FOREIGN PATENT DOCUMENTS

DE    2831553    1/1980

(Continued)

OTHER PUBLICATIONS

Instruction Manual for eflow® Electronic Nebulizer, © 2004 PARI Aerosol Research Institute.

(Continued)

*Primary Examiner* — Jason Boeckmann
(74) *Attorney, Agent, or Firm* — Clark Hill PLC

(57) ABSTRACT

A liquid dispensing device using a piezoelectric member in connection with an atomizing head and a passive metering method to supply liquid to the atomizing head. Preferably, the device is used to but not limited to dispensing of fragrances, insecticides or other aromatic solutions. The piezoelectric member does not vibrate the nozzle plate through which the liquid is dispensed. The passive metering method relies only on surface tension forces within the supply passageway. The device can work with a wider range of liquid properties than existing piezoelectric devices of this type. The passive metering method is robust and consistent, enabling larger and more varied liquid reservoirs because the reservoir height is not a factor in determining the performance of the device. The atomizing head functions with a wider range of liquids than atomizers whose nozzle plates are directly excited.

27 Claims, 6 Drawing Sheets

U.S. PATENT DOCUMENTS

| | | | |
|---|---|---|---|
| 3,901,443 | A | 8/1975 | Mitsui et al. |
| 3,912,953 | A | 10/1975 | Edoardo |
| 3,958,249 | A | 5/1976 | DeMaine et al. |
| 4,005,435 | A | 1/1977 | Lundquist et al. |
| 4,005,440 | A | 1/1977 | Amberntsson et al. |
| 4,007,464 | A | 2/1977 | Bassous et al. |
| 4,036,919 | A | 7/1977 | Komendowski et al. |
| 4,052,004 | A | 10/1977 | Martin et al. |
| 4,085,893 | A | 4/1978 | Durley, III |
| 4,113,809 | A | 9/1978 | Abair et al. |
| 4,153,201 | A | 5/1979 | Berger et al. |
| 4,158,847 | A | 6/1979 | Heinzl et al. |
| 4,161,670 | A | 7/1979 | Kern |
| 4,193,009 | A | 3/1980 | Durley, III |
| 4,206,160 | A | 6/1980 | Suddendorf et al. |
| 4,209,794 | A | 6/1980 | Kattner |
| 4,223,242 | A | 9/1980 | Redlich et al. |
| 4,240,081 | A | 12/1980 | Devitt |
| 4,251,031 | A | 2/1981 | Martin et al. |
| 4,261,512 | A | 4/1981 | Zierenberg |
| 4,294,407 | A | 10/1981 | Reichl et al. |
| 4,308,546 | A | 12/1981 | Halasz |
| 4,319,155 | A | 3/1982 | Nakai et al. |
| 4,337,896 | A | 7/1982 | Berger et al. |
| 4,338,576 | A | 7/1982 | Takahashi et al. |
| 4,339,763 | A | 7/1982 | Kyser et al. |
| 4,352,459 | A | 10/1982 | Berger et al. |
| 4,356,528 | A | 10/1982 | Coffee |
| 4,368,476 | A | 1/1983 | Uehara et al. |
| 4,380,018 | A | 4/1983 | Andoh et al. |
| 4,381,533 | A | 4/1983 | Coffee |
| 4,388,627 | A | 6/1983 | Umezawa |
| 4,402,458 | A | 9/1983 | Lierke et al. |
| 4,410,139 | A | 10/1983 | Nishikawa et al. |
| 4,413,268 | A | 11/1983 | Bentin |
| 4,418,354 | A | 11/1983 | Perduijn |
| 4,421,706 | A | 12/1983 | Feenstra et al. |
| 4,422,082 | A | 12/1983 | Louzil |
| 4,428,531 | A | 1/1984 | Martin |
| 4,431,136 | A | 2/1984 | Janner et al. |
| 4,465,234 | A | 8/1984 | Maehara et al. |
| 4,473,187 | A | 9/1984 | Lierke et al. |
| 4,474,326 | A | 10/1984 | Takahashi |
| 4,476,515 | A | 10/1984 | Coffee |
| 4,479,609 | A | 10/1984 | Maeda et al. |
| 4,513,297 | A | 4/1985 | Okamura |
| 4,528,577 | A | 7/1985 | Cloutier et al. |
| 4,530,464 | A | 7/1985 | Yamamoto et al. |
| 4,533,082 | A | 8/1985 | Maehara et al. |
| 4,533,735 | A | 8/1985 | Walter |
| 4,537,354 | A | 8/1985 | Eith |
| 4,539,575 | A | 9/1985 | Nilsson |
| 4,540,123 | A | 9/1985 | Junger et al. |
| 4,542,389 | A | 9/1985 | Allen |
| 4,546,361 | A | 10/1985 | Brescia et al. |
| 4,550,325 | A | 10/1985 | Viola |
| 4,550,326 | A | 10/1985 | Allen et al. |
| 4,564,297 | A | 1/1986 | Firth |
| 4,578,687 | A | 3/1986 | Cloutier et al. |
| 4,582,654 | A | 4/1986 | Karnicky et al. |
| 4,583,686 | A | 4/1986 | Martens et al. |
| 4,591,883 | A | 5/1986 | Isayama |
| 4,605,167 | A | 8/1986 | Maehara |
| 4,629,478 | A | 12/1986 | Browner et al. |
| 4,630,072 | A | 12/1986 | Scardovi et al. |
| 4,632,311 | A | 12/1986 | Nakane et al. |
| 4,641,053 | A | 2/1987 | Takeda |
| 4,659,014 | A | 4/1987 | Soth et al. |
| 4,667,877 | A | 5/1987 | Yao et al. |
| 4,689,515 | A | 8/1987 | Benndorf et al. |
| 4,696,719 | A | 9/1987 | Bischoff |
| 4,702,414 | A | 10/1987 | Hirabayashi et al. |
| 4,702,418 | A | 10/1987 | Carter et al. |
| 4,703,213 | A | 10/1987 | GaHerbert |
| 4,723,708 | A | 2/1988 | Berger et al. |
| 4,726,523 | A | 2/1988 | Kokubo et al. |
| 4,732,322 | A | 3/1988 | Gaysert et al. |
| 4,742,810 | A | 5/1988 | Anders et al. |
| 4,746,067 | A | 5/1988 | Svoboda |
| 4,752,422 | A | 6/1988 | Uchida et al. |
| 4,756,478 | A | 7/1988 | Endo et al. |
| 4,776,990 | A | 10/1988 | Verity |
| 4,783,003 | A | 11/1988 | Hirabayashi et al. |
| 4,784,323 | A | 11/1988 | Miller |
| 4,790,479 | A | 12/1988 | Matsumoto et al. |
| 4,793,339 | A | 12/1988 | Matsumoto et al. |
| 4,799,622 | A | 1/1989 | Ishikawa et al. |
| 4,815,661 | A | 3/1989 | Anthony |
| 4,828,886 | A | 5/1989 | Hieber |
| 4,842,493 | A | 6/1989 | Nilsson |
| 4,865,006 | A | 9/1989 | Nogi et al. |
| 4,877,989 | A | 10/1989 | Drews et al. |
| 4,888,516 | A | 12/1989 | Daeges et al. |
| 4,941,618 | A | 7/1990 | Hildebrand et al. |
| 5,011,632 | A | 4/1991 | Yano et al. |
| 5,021,701 | A | 6/1991 | Takahashi et al. |
| 5,152,456 | A * | 10/1992 | Ross et al. ............... 239/102.2 |
| 5,164,740 | A | 11/1992 | Ivri |
| 5,173,274 | A | 12/1992 | Owen |
| 5,217,165 | A | 6/1993 | Takahashi et al. |
| 5,261,601 | A | 11/1993 | Ross et al. |
| 5,297,734 | A | 3/1994 | Toda |
| 5,299,739 | A | 4/1994 | Takahashi et al. |
| 5,312,280 | A | 5/1994 | Kloba et al. |
| 5,312,281 | A | 5/1994 | Takahashi et al. |
| 5,343,122 | A | 8/1994 | Sugimori et al. |
| 5,355,158 | A | 10/1994 | Inada et al. |
| 5,518,179 | A | 5/1996 | Humberstone et al. |
| 5,529,055 | A | 6/1996 | Gueret |
| 5,586,550 | A | 12/1996 | Ivri et al. |
| 5,601,235 | A | 2/1997 | Booker et al. |
| 5,609,919 | A | 3/1997 | Yuan et al. |
| 5,657,926 | A | 8/1997 | Toda |
| 5,716,002 | A | 2/1998 | Haack et al. |
| 5,758,637 | A | 6/1998 | Ivri et al. |
| 5,803,362 | A | 9/1998 | Fraccaroli |
| 5,815,177 | A | 9/1998 | Sasaki |
| 5,823,428 | A | 10/1998 | Humberstone et al. |
| 5,894,001 | A | 4/1999 | Hitzler et al. |
| 5,921,232 | A | 7/1999 | Yokoi et al. |
| 5,927,618 | A | 7/1999 | Jefferies et al. |
| 5,938,117 | A | 8/1999 | Ivri |
| 6,014,970 | A | 1/2000 | Ivri et al. |
| 6,293,474 | B1 | 9/2001 | Helf et al. |
| 6,296,196 | B1 | 10/2001 | Denen et al. |
| 6,341,732 | B1 | 1/2002 | Martin et al. |
| 6,378,780 | B1 | 4/2002 | Martens, III et al. |
| 6,382,522 | B2 | 5/2002 | Tomkins et al. |
| 6,386,462 | B1 | 5/2002 | Martens, III |
| 6,439,474 | B2 | 8/2002 | Denen |
| 6,446,880 | B1 | 9/2002 | Schram et al. |
| 6,450,419 | B1 | 9/2002 | Martens, III et al. |
| 6,482,863 | B2 | 11/2002 | Munagavalasa et al. |
| D471,087 | S | 3/2003 | McCoy et al. |
| 6,706,988 | B1 | 3/2004 | Helf et al. |
| 6,752,327 | B2 | 6/2004 | Martens, III et al. |
| 6,786,427 | B2 | 9/2004 | Schram et al. |
| 6,789,741 | B2 | 9/2004 | Varanasi et al. |
| 6,793,149 | B2 | 9/2004 | Schramm et al. |
| 6,843,430 | B2 | 1/2005 | Boticki et al. |
| 6,857,580 | B2 | 2/2005 | Walter et al. |
| 6,896,193 | B2 | 5/2005 | Helf et al. |
| 7,017,829 | B2 | 3/2006 | Martens, III et al. |
| 7,070,121 | B2 | 7/2006 | Schramm et al. |
| 7,669,782 | B2 * | 3/2010 | Wang et al. ............... 239/102.1 |
| 8,113,204 | B2 * | 2/2012 | Koerner et al. ........... 128/207.14 |
| 2001/0022024 | A1 | 9/2001 | Takeuchi et al. |
| 2002/0144678 | A1 | 10/2002 | Warby |
| 2002/0175220 | A1 * | 11/2002 | Pence ....................... 239/102.2 |
| 2004/0195352 | A1 * | 10/2004 | Koerner et al. ........... 239/102.1 |
| 2008/0073447 | A1 * | 3/2008 | Wang et al. .................... 239/302 |
| 2008/0099572 | A1 | 5/2008 | Tollens et al. |

FOREIGN PATENT DOCUMENTS

| | | |
|---|---|---|
| DE | 3434111 | 3/1986 |
| DE | 3608205 | 9/1987 |
| DE | 3734905 | 5/1989 |

| | | |
|---|---|---|
| EP | 0049636 | 4/1982 |
| EP | 0134847 | 3/1985 |
| EP | 0207568 | 1/1987 |
| EP | 0432992 | 6/1991 |
| EP | 0480615 | 4/1992 |
| EP | 0897755 | 2/1999 |
| GB | 1177623 | 1/1970 |
| GB | 1454597 | 11/1976 |
| GB | 2041249 | 9/1980 |
| JP | 55-082245 | 6/1980 |
| JP | 57-105608 | 1/1982 |
| JP | 58-062411 | 4/1983 |
| JP | 58-109156 | 6/1983 |
| JP | 59-203661 | 11/1984 |
| JP | 60-004714 | 1/1985 |
| JP | 01-108049 | 4/1989 |
| JP | 01-150725 | 6/1989 |
| WO | WO 92/11050 | 7/1992 |
| WO | WO 96/31289 | 10/1996 |
| WO | WO 00/58709 | 10/2000 |
| WO | WO 2006/127181 | 11/2006 |

OTHER PUBLICATIONS

Dr. Stefan Seemann, "Delivering Macromolecules by Nebulization—from Proof of Concept to Commercialization", 2007 National Biotechnology Conference, Pari Pharma, Munich, Germany.

* cited by examiner

LIQUID DISPENSING APPARATUS USING A PASSIVE LIQUID METERING METHOD

CROSS-REFERENCE AND INCORPORATION BY REFERENCE

This patent application claims the benefit of domestic priority of U.S. Provisional Application Ser. No. 61/073,275, filed Jun. 17, 2008, and entitled "Liquid Dispensing Apparatus Using A Passive Liquid Metering Method". U.S. Provisional Application Ser. No. 61/073,275 is hereby incorporated by reference in its entirety.

FIELD OF THE INVENTION

The subject invention relates generally to liquid dispensing devices and, more particularly, to liquid dispensing devices using piezoelectric actuation and passive metering methods.

BACKGROUND OF THE INVENTION

Devices exist to atomize and dispense liquids. These include liquid dispensers, medical devices, printing devices and many more. Pressurized aerosol canisters and hand-operated sprayers are the most common devices in use. Pressurized devices have environmental concerns related to volatile emissions and are also limited by precision metering of liquids, cost and power consumption.

Piezoelectric ultrasonic vaporization devices have been developed to increase precision, especially for printing and medical device applications. Some devices, such as used in a humidifier, are less precise and work only with certain types of liquids.

Other piezoelectric ultrasonic devices for liquid dispensing use a vibrating membrane and a wick to deliver liquid to the vibrating membrane. The wick limits the range of liquids to be used in these devices because of clogging of the wick and limitations of the viscosity of the liquid. The vertical orientation of a wick further restricts the design because it requires that the orientation of the vibrating membrane be horizontal. Further, the vibrating membrane in such devices is sensitive to residual accumulation of liquid on the plate. This reduces the range of liquids that can be used in such a device. Finally, the reservoir size that can be used in such a device is relatively small, because its height is limited by the height that a wick can draw liquid to the vibrating membrane.

Devices used to dispense ink for printing employ a chamber pressurized from the back to eject droplets through a perforated membrane. These designs are appropriate for Inkjet printing but are relatively expensive because they require precise semiconductor fabrication processes. In such designs, the delivery of liquid to the perforated membrane is a challenge and only small volume reservoirs can be used.

SUMMARY OF THE INVENTION

The present invention is an improved device to atomize and dispense liquids.

One embodiment of the present invention is focused on dispensing fragrances, perfumes, insecticides or other related aromatic solutions.

One embodiment of the present invention features an atomizing head consisting of several plates forming a small chamber of liquid. A vibrating plate that is actuated by a piezoelectric device attached to the vibrating plate compresses the chamber. The pressurized liquid is atomized as it is dispensed through a perforated membrane on the first planar member.

The advantage of this design is that the device is less sensitive to the liquid properties because it directly compresses liquid in the chamber. This is an advantage compared to devices that directly vibrate the perforated membrane plate, which are more sensitive because they rely on liquid inertia to propel the liquid and therefore depend on the liquid properties, especially including viscosity and specific gravity.

One embodiment of the present invention incorporates a new method for delivering liquid to the atomizer head. The device consists of a large liquid reservoir with a downward-pointing tube. The tube allows liquid to fall into a small liquid reservoir. An air lock between the liquid level in the small reservoir and the tube automatically maintains the desired liquid height in the small reservoir and the tube automatically maintains the desired liquid height in the small reservoir. Surface tension forces draw the liquid from the small reservoir automatically to the atomizer head with a controlled backpressure. This system provides passive metering of liquid to the atomizing head and is passive, simple and low-cost. Another advantage of this design is that there is no restriction on the size of the large reservoir.

This embodiment of the present invention requires no pressurized gas propellant (VOC's), which are increasingly regulated by both State and Federal Agencies, thereby eliminating environmental challenges associated with such aerosol devices.

BRIEF DESCRIPTION OF THE DRAWINGS

The features of the illustrated embodiment of the invention, which are novel, are described in detail herein below. The organization and manner of the structure and operation of the invention, together with further objects and advantages thereof, may best be understood by reference to the following description and viewed in connection with the accompanying drawings wherein like reference numerals identify like elements in which.

DETAILED DESCRIPTION OF THE ILLUSTRATED EMBODIMENTS

For purposes of the description hereinafter, the words “upper”, “lower”, “right”, “left”, “vertical”, “horizontal”, “top”, “bottom”, “lateral”, “longitudinal”, “small”, “large” and like spatial terms, if used, shall relate to the described embodiments as oriented in the figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

While specific embodiments of the invention have been described in detail, it will be appreciated by those skilled in the art that various modifications and alternatives to those details could be developed in light of the overall teachings of the disclosure. The presently preferred embodiments described herein are meant to be illustrative only and not limiting as to the scope of the invention which is to be given the full breadth of the appended claims and any and all equivalents thereof. For example, while the present invention is implemented primarily from the point of view of dispensing liquids containing liquids in the described embodiments, the present invention may also be effectively implemented on, for example, but not so limited to, printing, chemical dispersion on production lines, etc.

The present invention vaporizes and dispenses liquid without the use of compressed gas propellants, achieving environmental benefits. The present invention is more robust in its liquid delivery method compared to ultrasonic piezoelectric devices employing wicks. Accordingly, the device can work with a wider range of liquid properties than existing piezoelectric devices of this type. The passive metering function is robust and consistent, enabling larger and more varied liquid reservoirs because the reservoir height is not a factor in determining the performance of the device. The atomizer head with a chamber excited on its second planer member functions with a wider range of liquids than atomizers whose membrane plate is directly excited.

FIG. 1 is an image of a preferred embodiment of the present invention. The exterior housing 1 is preferably a plastic injection-molded part that serves as a housing for the internal components, a mounting structure, and includes the external shape features for the liquid dispensing apparatus. The exterior housing incorporates a printed circuit board (PCB) 2. The PCB performs computations and provides an interface to the user controls that can allow for changes to the time and duration of the duty cycle for dispensing the liquid, which may or may not be co-located on the backside of the PCB, accessible through the exterior housings via depressible buttons, switches or other controls. The PCB 2 contains a signal generator module that generates a specific oscillating voltage signal to excite the piezoelectric liquid dispensing apparatus. The PCB also contains power amplifier components to amplify the signal to the appropriate voltage and current necessary to drive the piezoelectric atomizing device, all of which circuitry is well known in the art. In some embodiments, the invention may comprise several printed circuit boards electrically connected via wires to perform the needed functions. A liquid reservoir 3 is mounted inside the exterior housing 1. The liquid reservoir contains the liquid or other liquid to be dispensed into the air by the device. It should be noted that the liquid reservoir 3 is not a pressure vessel and is not pressurized with propellant, differentiating it from aerosol reservoirs. The liquid reservoir 3 is equipped with an outlet fitting 3' that is sealed during shipping with a seal made of foil, plastic film, cap or other material. During replacement of a liquid reservoir, it is oriented such that the outlet fitting 3' faces downward and is inserted onto a tube 5', providing a seal between the reservoir 3 and the tube 5' and providing a path for liquid to flow into the second reservoir 7 (see FIG. 2). The exterior housing 1 also contains a power supply, preferably two AA-cell, C-cell or D-cell batteries 4.

FIG. 2 is an exploded view of the liquid dispensing apparatus 5. The bottom of the liquid reservoir 3 is shown in its orientation during installation and during use. The tube 5' of the liquid dispensing apparatus 5 penetrates the seal of the large liquid reservoir 3 during replacement or installation. The large liquid reservoir 3 has low gas permeability to air. Upon installation, the large reservoir 3 is connected with the tube 5' to provide an airtight seal. The large reservoir 3 must be sufficiently rigid so that it will not deform from pressure changes while the device is in operation. This allows liquid to feed via gravity into a second, smaller reservoir 7. The liquid level of the second reservoir 7 is automatically and passively controlled with pressure forces created by the pressure within the second reservoir 7 once the liquid level of the second reservoir 7 fills to a level that prevents the passage of air into the tube 5' and liquid reservoir 3 as best understood with reference to FIG. 3. During operation, liquid is drawn out of the second reservoir 7, lowering its level. When the level drops to the point where the liquid level is below the bottom of the tube 5', air enters the liquid reservoir 3 and additional liquid moves via gravity forces from the liquid reservoir 3 into the second reservoir 7. This process fills the second reservoir 7 until the level is once again equal to or higher than the bottom edge of the tube 5', sealing off the flow of air and achieving a new pressure equilibrium. This process occurs automatically until the liquid reservoir 3 is emptied of its liquid. An essential feature of this operation is that the level of the liquid in the second reservoir 7 is maintained with only a small fluctuation. This enables a near-constant supply of liquid to be delivered to the atomizing head 6 at a constantly maintained level and pressure, which is important with respect to preventing unwanted leakage through the atomizing head, as will be more fully understood upon reading the discussion below.

Figure 1:
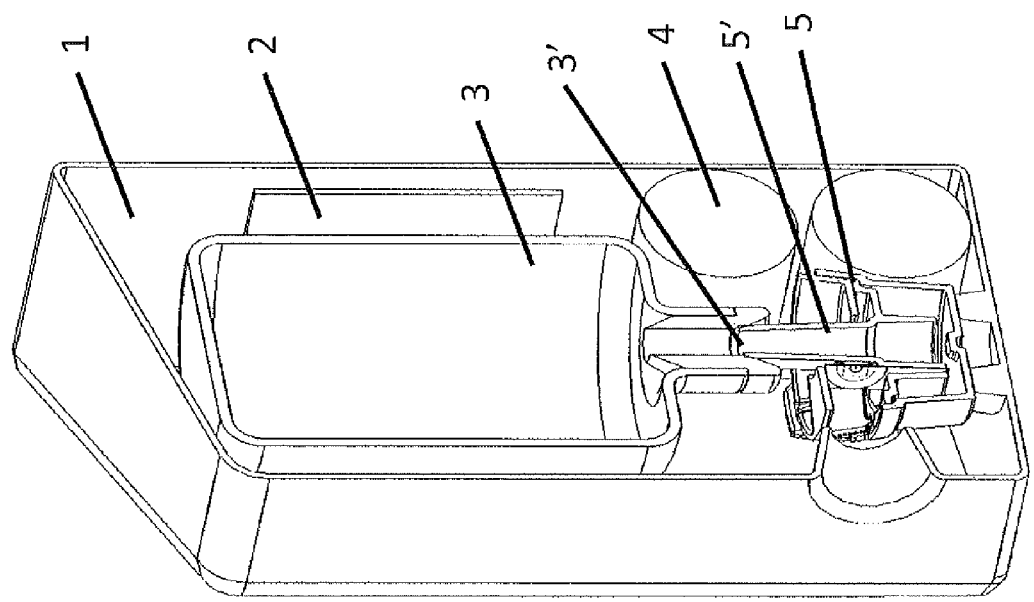
FIG. 1 shows a device for dispensing atomized liquid. The exterior housing 1 preferably is a plastic injection-molded part that serves as a housing for the internal components, a mounting structure, and includes the desirable external shape features for the liquid dispensing apparatus 5 and tube 5'. The exterior housing incorporates a control printed circuit board (PCB) 2. The large liquid reservoir 3 is mounted inside the exterior housing 1. The exterior housing also contains a power supply, preferably two AA-cell, C-cell or D-cell batteries 4.
Figure 2:
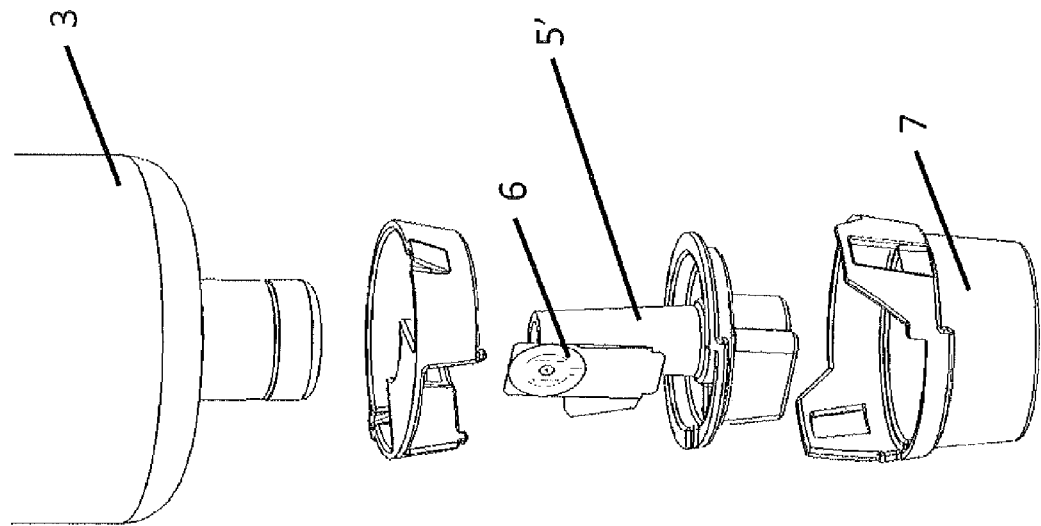
FIG. 2 is an exploded view of the liquid dispensing apparatus 5. The exploded view shows the large liquid reservoir 3, located adjacent to the liquid dispensing apparatus 5, which supplies liquid to the smaller reservoir 7. The atomizing head 6 is seated in the assembly via a spring loading of the atomizing head's planar members.
Figure 3:
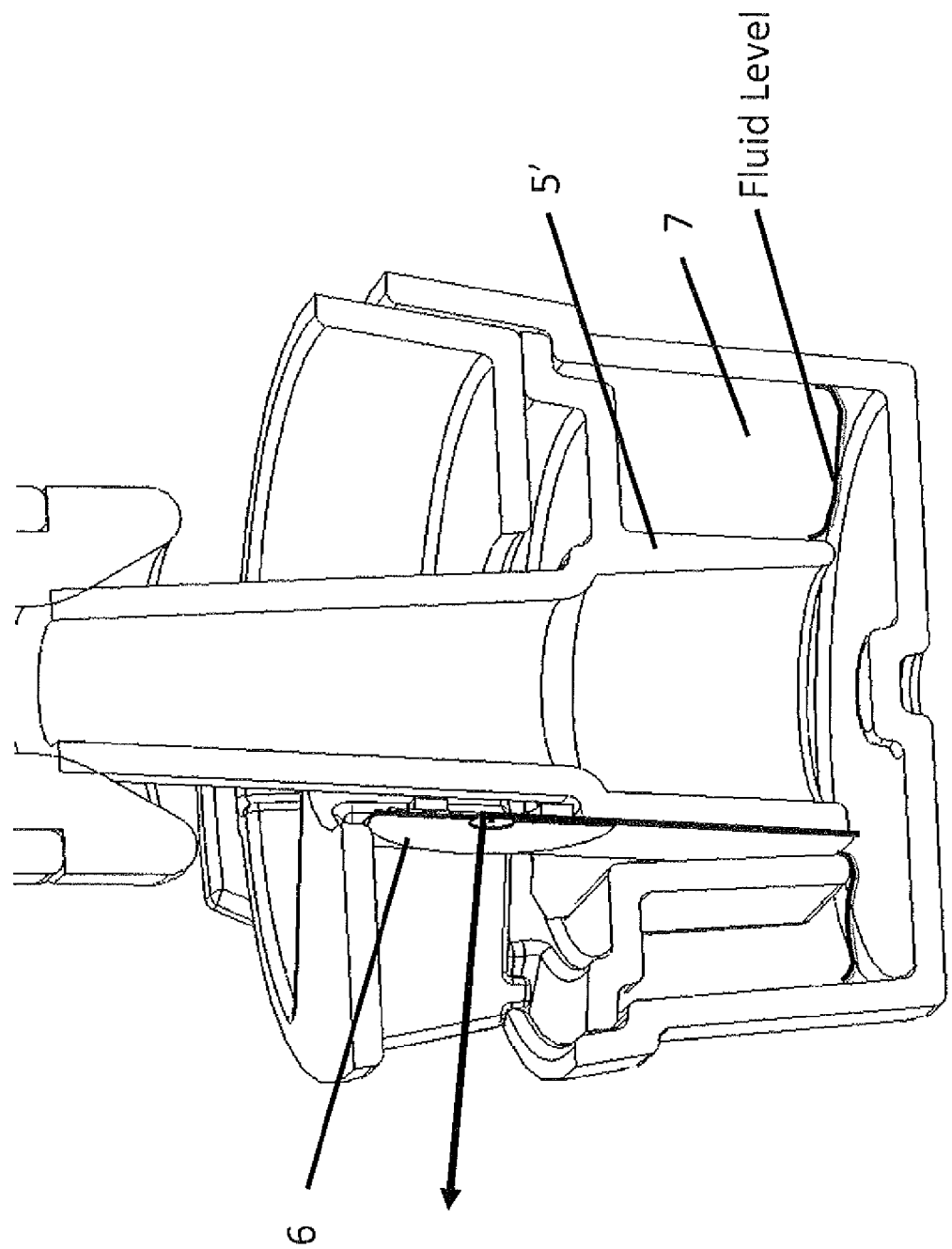
FIG. 3 shows a side-view cross section of the liquid dispensing apparatus 5. The second reservoir 7 maintains a supply of liquid that is delivered to an atomizing head 6. The tube 5' provides a pathway for the liquid to flow from the large liquid reservoir 3 to the smaller reservoir 7. The bottom edge of the tube 5' limits the liquid level so the atomizing head 6 is supplied with a constant liquid level. The geometry formed by the planar features of the atomizing head 6 and the curved tube 5' outer surface provides a means for the surface tension forces to deliver liquid from the small reservoir 7 to the chamber in the atomizing head 6.

FIG. 3 shows a side-view cross section of the liquid dispensing apparatus 5. The second reservoir 7 maintains a supply of liquid that is delivered to an atomizing head 6. The liquid level in the second reservoir 7 is maintained at or very near to the height of the bottom of the tube 5'. Liquid is passively delivered upward from the bottom edge of the spacer plate 10 to the upper region of the atomizing head 6 by way of surface tension forces. Surface tension in the liquid that is responsible for transporting the liquid upward against the force of gravity is established by the geometry formed between the back side of the planar atomizing head spacer plate 10 and the curved exterior surface of the tube 5'.

Figure 3A:
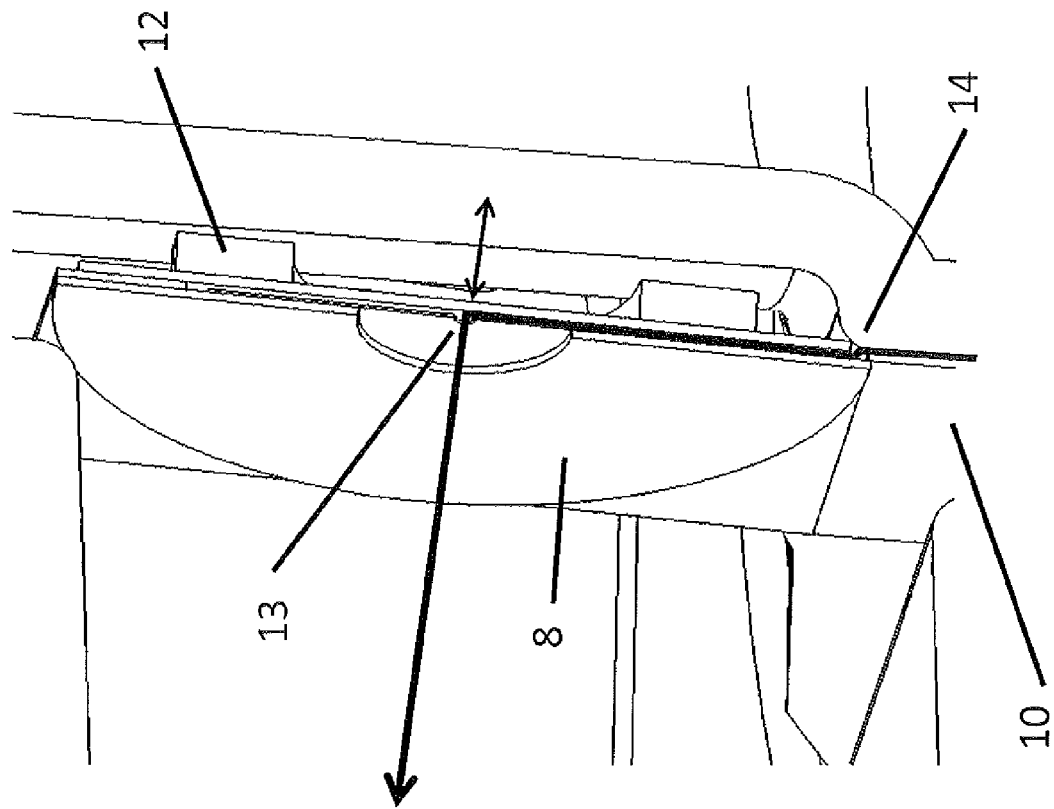
FIG. 3a shows a side-view cross section of the liquid dispensing apparatus 5 and the atomizing head 6.

FIG. 3a shows a side-view cross section of the liquid dispensing apparatus 5 and the atomizing head 6. The liquid that is drawn upward by surface tension in the region between the planar spacer plate 10 and the curved exterior surface of the tube 5' is further drawn upward from the bottom circumferential edge of the second planar member and into the liquid chamber via a small opening at the bottom of the liquid chamber. The opening is defined by a notch 14 (see FIG. 4) at the bottom edge of the hole in the spacer plate 10 and the first and second planar members. The passage defined by the exterior surface of tube 5' and the particular geometry in the atomizing head 6 enables liquid to reach the apertures 13 in the atomizing head 6 without the need for a capillary tube or wick.

Figure 4:
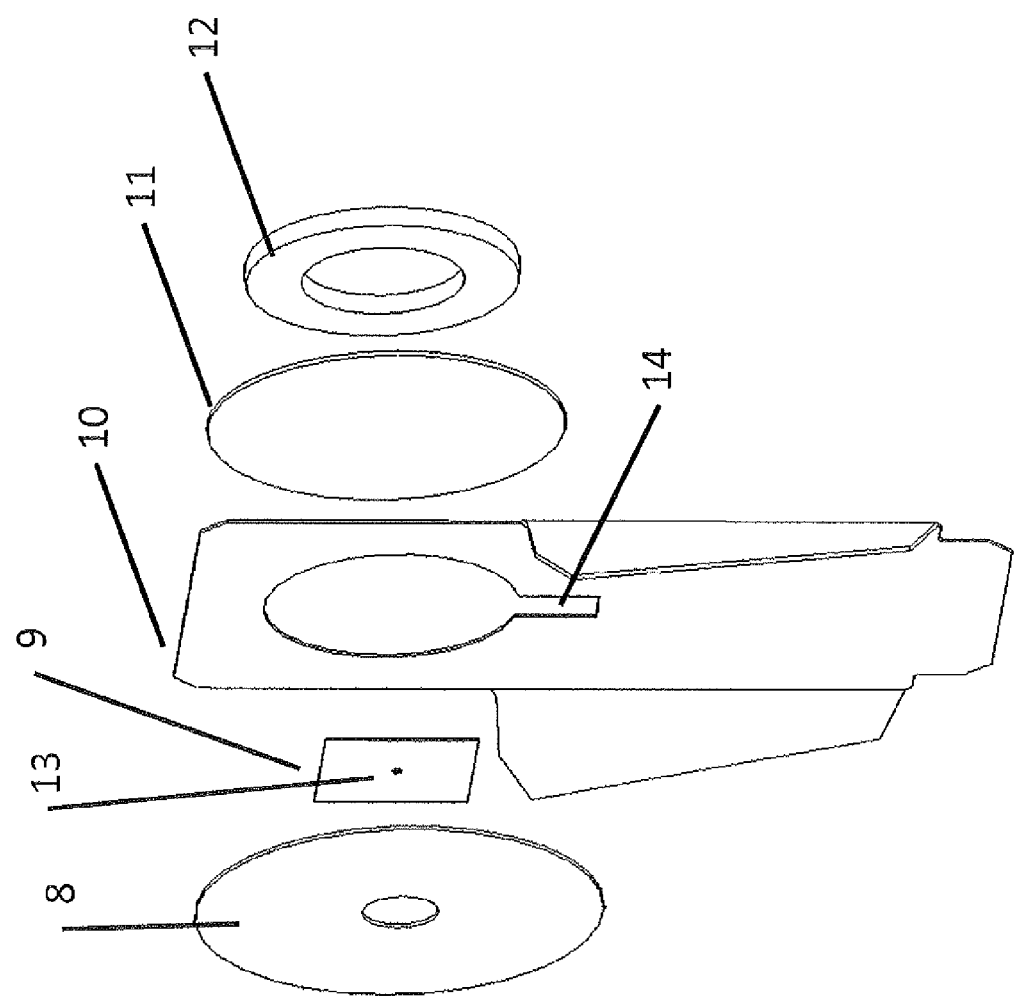
FIG. 4 shows a close-up exploded view of the atomizing head 6. The atomizing head 6 comprises several planar members and other components that are affixed to each other, preferably using a solder-bond process. As illustrated, a first planar member 8 is a cylindrical plate. The first planar member 8 includes an aperture plate 9, which contains nozzle-shaped holes 13. For purposes of explanation only, once affixed, the aperture plate 9 is then considered an integral part of the first planar member 8. The first planar member 8 is affixed to a spacer plate 10. The spacer plate 10 also serves to prescribe the axial distance between the first planar member 8 and a second planar member 11. The atomizing head assembly provides a means for rigidly supporting the thin aperture plate 9, a resonant actuator for pumping the liquid, and a liquid cavity from which to dispense liquid. A notch 14 at the bottom edge of the hole located in the spacer plate 10 provides a portion of the pathway for the liquid to be drawn into the liquid cavity. A piezoelectric ring 12 is affixed to the back of the second planar member 11.

FIG. 4 shows a close-up exploded view of the atomizing head 6. The atomizing head consists of several planar members and other components that are affixed to each other, preferably using a solder-bond process. The planar members can also be affixed together using laser or spot welding, sheet metal forming of one or more planar members, or additional parts including a plastic housing. A first planar member 8 is preferably a cylindrical plate made of stainless steel or brass, depending on the liquid application. The first planar member 8 includes an aperture plate 9, which contains preferably 10 to 200 nozzle-shaped holes. The holes are tapered from the back to the front of the aperture plate and are preferably sized between 5 to 20 um in diameter at their smallest dimension. The aperture plate 9 is fabricated preferably using an electro forming process with a nickel alloy or other metal compatible with the electro forming process. The aperture can also be fabricated using a laser abolition process. Its size and shape are tailored to minimize production costs. Once affixed, the aperture plate 9 is considered for purposes of this discussion to be an integral part of the first planar member 8. The first planar member 8 is affixed to a spacer plate 10. The base of the spacer plate serves as the base of the atomizing head 6. The spacer plate 10 also serves to prescribe the axial distance between the first planar member 8 and a second planar member 11. This distance is important to the structural vibration and fluid dynamics of the device, and is preferably between 25 and 100 um. The second planar member 11 (also sometimes referred to as the resonator plate) is affixed to the back of the spacer plate 10. Once assembled with the first and second planar members, together with the circular hole in the spacer plate 10 forms a very small chamber from which a volume of liquid is dispensed. The liquid drawn up to the upper region of the atomizing head 6 using surface tension enters the small liquid chamber through an opening formed by a notch 14 at the bottom edge of the hole in the spacer plate 10. A piezoelectric ring 12 is affixed to the back of the second planar member 11. This piezoelectric ring is preferably solder bonded to the second planar member with a low temperature solder so as to not depole the piezoelectric material. The piezoelectric material is poled along the symmetric axis of the piezoelectric ring. The voltage is applied between an electrode on the back surface of the piezoelectric ring and the electrically conductive second planar member. Voltage with the same sense as the piezoelectric poling direction generates an electric field in the piezoelectric material such that the piezoelectric ring contracts radially and circumferentially, but extends axially. Voltage with an opposite sense to that of the poling direction will generate an inverse deflection in the piezoelectric material. Piezoelectric coupling in this configuration is characterized by the $d_{31}$ constant. During operation, oscillating voltage is applied to the piezoelectric ring, causing it to oscillate at the corresponding frequency. These contractions and expansions result in an oscillating stress at the interface between the piezoelectric ring and the second planar member 11. The oscillating stress creates vibrations of the second planar member 11 at a frequency corresponding to its structural resonance. This creates amplified vibrations, which generate oscillating pressure in the small volume of liquid between the first and second planar members. The combination of motion and pressure atomizes the liquid as it passes through the apertures 13 in the first planar member 8, and provides the liquid with sufficient velocity such that it is ejected from the atomizer head 6 in a direction normal to the surface of the first planar member such that it travels a sufficient distance from the external housing 1. Traveling a sufficient distance prevents liquid from landing on the external housing 1, and, in the case of fragrance, improves the dispersion of the fragrance through the air. In a preferred embodiment of the atomizer head 6, the region in which the first planar member 8 is located is oriented at an angle such that the vector defined by the liquid ejection relative to a horizontal plate forms a 0 to 60 degree angle. Changing the orientation of the entire atomizer head 6, or introducing a bend in the spacer plate 10 at a location below the first planar member 8 can achieve this. An additional feature of the embodiment of the invention is that it allows for long-term or constant operation of the liquid dispenser. This is achieved because the atomization is robust and does not depend on formation of a film or residue of liquid on the first planar member 8, as is the case in devices of the prior art.

Figure 5:
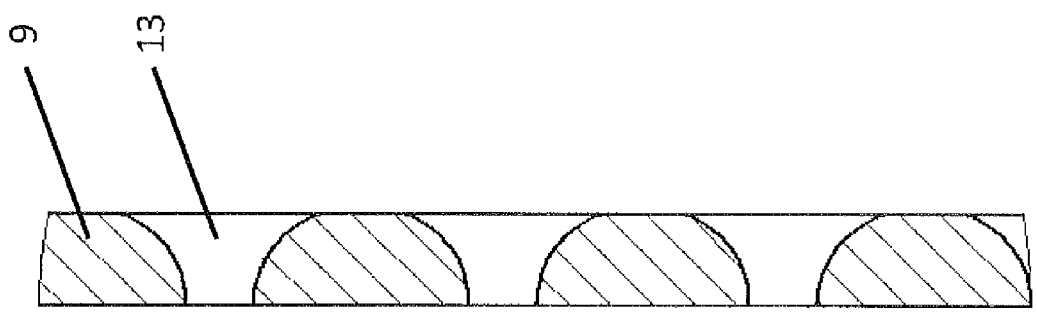
FIG. 5 shows a close-up cross section view of tapered holes 13 in the aperture plate 9. The tapered apertures 13 are a series of holes that provide a means for the liquid particles to be atomized and projected through the first planar member 8.

FIG. 5 shows a close-up cross section view of tapered holes 13 formed in the aperture plate 9. The structure of the aperture plate 9 is shown shaded. The tapered apertures 13 are a series of holes that provide a means for the liquid particles to be atomized and projected through the first planar member 8.

While preferred embodiments of the present invention are shown and described, it is envisioned that those skilled in the art may devise various modifications of the present invention without departing from the spirit and scope of the appended claims.

The invention is claimed as follows:

1. An atomizing head for use in a liquid dispensing device, said atomizing head comprising:

first and second members which each have front and rear planar surfaces, said first member has an aperture which extends therethrough from said front planar surface thereof to said rear planar surface thereof;

at least one nozzle associated with said first member for dispersing liquid;

a piezoelectric member affixed to said rear planar surface of said second member;

a first plate having front and rear planar surfaces, said front planar surface of said first plate being affixed to said rear planar surface of said first member, said rear planar surface of said first plate being affixed to said front surface of said second member, said first plate defining an aperture therethough, said aperture of said first plate defining a liquid chamber which is defined between said first and second members, said at least one nozzle being in fluid communication with said liquid chamber; and a second plate having front and rear surfaces, said second plate having at least one hole which extends therethrough from said front surface to said rear surface, said front surface of said second plate being affixed to said rear planar surface of said first member in such a manner that said at least one hole defined by said second plate is in fluid communication with said aperture defined by said first member, said at least one hole of said second plate defining said at least one nozzle associated with said first member, said second plate being positioned within said aperture of said first plate and further defining said liquid chamber.

2. The atomizing bead as defined in claim 1, wherein said second plate has approximately 10 to 200 holes extending therethrough.

3. The atomizing head as defined in claim 1, wherein said at least one hole extending through said second plate has a smallest diameter of approximately 5 to 20 um.

4. The atomizing head as defined in claim 1, wherein said first member is a cylindrical plate.

5. The atomizing head as defined in claim 1, wherein said first plate defines an axial distance between said first member and said second member.

6. The atomizing head as defined in claim 5, wherein said axial distance between said first member and said second member is approximately 25 to 100 um.

7. The atomizing head as defined in claim 1, wherein said aperture provided through said first plate is generally circular in configuration.

8. The atomizing head as defined in claim 1, wherein said aperture provided through said first plate defines a notch at a lower end thereof, said notch being positioned below said first and second members in order to allow liquid to enter said liquid chamber via said notch.

9. The atomizing head as defined in claim 1, wherein said second member is a solid cylindrical plate.

10. The atomizing head as defined in claim 1, wherein said piezoelectric member is in the shape of a ring.

11. The atomizing head as defined in claim 1, wherein said nozzles are tapered in configuration.

12. An atomizing head for use in a liquid dispensing device, said atomizing head comprising:

a first member having a front surface and a rear planar surface, the first member defining an aperture which extends therethrough from the front surface to the rear planar surface;

a second member having a front planar surface and a rear surface;

a spacer member having front and rear planar surfaces, the spacer member being positioned between the first and second members with the front planar surface of the spacer member being affixed to the rear planar surface of the first member and with the rear planar surface of the spacer member being affixed to the front planar surface of the second member, the spacer member defining an aperture which extends therethrough from the front planar surface thereof to the rear planar surface thereof, the aperture of the spacer member defining a liquid chamber which is defined between the rear planar surface of the first member and the front planar surface of the second member;

a piezoelectric member affixed to the rear surface of the second member; and a plate member having a front planar surface and a rear surface, the front planar surface of the plate member being affixed to the rear planar surface of the first member and being sized to cover the aperture defined by the first member, the plate member being wholly positioned within the liquid chamber defined by the aperture of the spacer member, the rear surface of the plate member being separated from the front planar surface of the second member, the plate member defining at least one nozzle-shaped hole which extends therethrough from the front planar surface thereof to the rear surface thereof, the at least one nozzle-shaped hole of the plate member being in fluid communication with both the aperture of the first member and the liquid chamber, whereby activation of the piezoelectric member causes the second member to vibrate, thereby generating oscillating motion and pressure in liquid contained in the liquid chamber and causing the liquid to be atomized and dispersed through the at least one nozzle-shaped hole, through the aperture of the first member and outward beyond the front surface of the first member.

13. The atomizing head as defined in claim 12, wherein the front surface of the first member is planar.

14. The atomizing head as defined in claim 12, wherein the rear surface of the second member is planar.

15. The atomizing head as defined in claim 12, wherein the rear surface of the plate member is planar.

16. The atomizing head as defined in claim 12, wherein an axial distance between the front planar surface of the plate member and the rear surface of the plate member is between 25 and 100 um.

17. The atomizing head as defined in claim 12, wherein the at least one nozzle-shaped hole is tapered from the rear surface of the plate member to the front planar surface of the plate member.

18. The atomizing head as defined in claim 12, wherein the at least one nozzle-shaped hole has a minimum diameter of between 5 and 20 um.

19. The atomizing head as defined in claim 12, wherein the plate member has approximately 10 to 200 nozzle-shaped holes extending therethrough.

20. The atomizing head as defined in claim 12, wherein the piezoelectric member is in the shape of a ring.

21. The atomizing head as defined in claim 12, wherein the atomization and dispersion of the liquid through the at least one nozzle-shaped hole is not caused by a significant volume change of the liquid chamber.

22. The atomizing head as defined in claim 12, wherein the second member is formed of an electrically conductive material such that the second member vibrates when the piezoelectric member is vibrated.

23. The atomizing head as defined in claim 12, wherein the spacer member further has a delivery passageway provided therein for providing liquid to the liquid chamber, the liquid chamber being located above the delivery passageway.

24. The atomizing head as defined in claim 12, wherein the first member is a cylindrical plate.

25. The atomizing head as defined in claim 12, wherein the aperture provided through the spacer member is generally circular in configuration.

26. The atomizing head as defined in claim 12, wherein the aperture provided through the spacer member defines a notch at a lower end thereof, the notch being positioned below the first and second members in order to allow liquid to enter the liquid chamber via the notch.

27. The atomizing head as defined in claim 12, wherein the second member is a solid cylindrical plate.

* * * * *